US012773530B2

(12) United States Patent
Gallant et al.

(10) Patent No.: US 12,773,530 B2
(45) Date of Patent: Oct. 27, 2026

(54) SURGICAL CATHETER SNAP TOOL

(71) Applicant: Medivis, Inc., New York, NY (US)

(72) Inventors: Jesse Harrison Gallant, New York, NY (US); Christopher Morley, New York, NY (US); Osamah Choudhry, New York, NY (US); Long Qian, Brooklyn, NY (US)

(73) Assignee: Medivis, Inc., New York, NY (US)

( * ) Notice: Subject to any disclaimer, the term of this patent is extended or adjusted under 35 U.S.C. 154(b) by 318 days.

(21) Appl. No.: 18/244,335

(22) Filed: Sep. 11, 2023

(65) Prior Publication Data

US 2024/0238560 A1 Jul. 18, 2024

Related U.S. Application Data

(63) Continuation-in-part of application No. 18/097,858, filed on Jan. 17, 2023, now Pat. No. 12,578,546.

(51) Int. Cl.

| | |
|---|---|
| ***A61B 34/20*** | (2016.01) |
| ***A61M 25/01*** | (2006.01) |
| ***G06T 7/73*** | (2017.01) |

(52) U.S. Cl.

CPC ........... *A61M 25/0105* (2013.01); *G06T 7/73* (2017.01)

(58) Field of Classification Search

CPC ........................... A61M 25/0105; A61B 34/20

See application file for complete search history.

(56) References Cited

U.S. PATENT DOCUMENTS

| | | | | |
|---|---|---|---|---|
| 2016/0199148 A1* | 7/2016 | Maracaja-Neto | .... | A61B 1/0052 600/424 |
| 2019/0053860 A1* | 2/2019 | Corndorf | ............... | A61B 34/20 |
| 2019/0321599 A1* | 10/2019 | Burkholz | .......... | A61M 25/0606 |
| 2021/0322107 A1* | 10/2021 | Bratbak | ................. | A61B 34/20 |
| 2022/0168547 A1* | 6/2022 | Ma | .................... | A61M 25/0606 |
| 2022/0240909 A1* | 8/2022 | Schoen | .................. | A61B 17/00 |

* cited by examiner

*Primary Examiner* — Anne M Kozak
*Assistant Examiner* — Kaitlyn Eunji Kim
(74) *Attorney, Agent, or Firm* — Cognition IP, P.C.; Edward Steakley; Justin White

(57) ABSTRACT

A surgical catheter snap tool can include an elongated main body defining a longitudinal axis and having a front end, a back end, a top surface, first and second side surfaces, and a bottom surface. The elongated main body can include fiducial marker site(s) configured to host fiducial marker(s) at the top surface, a grip region at the first side surface, and a longitudinal groove oriented along the longitudinal axis at the bottom surface and extending from the front end to the back end. The longitudinal groove can be configured to snap onto and hold a surgical catheter therein. The tool can also include arm(s) extending laterally from the elongated main body that can have additional fiducial marker site(s). An overall system can include the surgical catheter snap tool, the fiducial markers, the surgical catheter, and/or a stylet slidably inserted within the surgical catheter.

20 Claims, 9 Drawing Sheets

SURGICAL CATHETER SNAP TOOL

CROSS-REFERENCE TO RELATED APPLICATIONS

This application a continuation-in-part of and claims priority to commonly owned U.S. patent application Ser. No. 18/097,858, filed on Jan. 17, 2023, and titled "SNAP ON MEDICAL INSTRUMENT FOR OPTICAL TRACKING," which application is hereby incorporated herein by reference in its entirety. This application is also related to commonly owned U.S. patent application Ser. No. 18/244,338 filed on Sep. 11, 2023 and titled "ADHESIVE SURGICAL REFERENCE MARKER UNIT," which application is also hereby incorporated herein by reference in its entirety.

TECHNICAL FIELD

The present disclosure relates generally to medical devices, and more particularly to surgical tools and devices used during medical procedures.

BACKGROUND

Planning and navigation are necessary for many medical procedures, such as live surgeries and also practice, training, planning, and developmental procedures. Surgical teams typically have a plan based on medical imagery before ever entering an operating room. Conventional medical imaging systems such as X-ray, MRI, CT, and others have limitations regarding two-dimensional and three-dimensional images, however, and surgeons often need to consider numerous image views and slices to plan surgical procedures. Recent medical advances leverage these applications of medical imagery and surgical plans by using a computer-aided augmented reality environment, which can allow for the tracking of patients and physical instruments during surgical procedures by using fiducial markers and tracking components.

Unfortunately, conventional tracking systems are often limited in their ability to accurately generate, render, and apply virtual interactions in an augmented reality environment based on the orientations and positions of physical instruments with respect to those of physical landmarks identified on a patient body, particularly when things move during surgery. Unstable or unreliable positioning of fiducial markers can play a role in these issues. Limited or inaccurate tracking can then affect the overall performance of such systems during surgical procedures, and the need for accuracy in this regard can lead to overly cumbersome or complex attachment devices and systems.

While traditional ways of virtually tracking items during surgery have worked well in the past, improvements are always helpful. In particular, what is desired are medical systems and devices that facilitate the stable and reliable positioning of fiducial markers during surgery in a simple and streamlined manner.

SUMMARY

It is an advantage of the present disclosure to provide medical systems and devices that facilitate the stable and reliable positioning of fiducial markers during surgery in a simple and streamlined manner. Various embodiments disclosed herein relate to features, apparatuses, systems, and methods of use for surgical tools configured for use with augmented reality systems. This can involve localizer tools configured for the positioning of fiducial markers during augmented reality aided surgery, as well as catheter tools configured for the steady handling of surgical catheters. In specific arrangements, this can involve surgical catheter snap tools that combine the ability to position fiducial markers locally relative to a patient while also facilitating the steady handling and positioning of a surgical catheter with the same device.

In various embodiments of the present disclosure, a surgical apparatus can include an elongated main body defining a longitudinal axis and having a front end, a back end, a top surface, first and second side surfaces, and a bottom surface. The elongated main body can include one or more fiducial marker sites configured to host fiducial markers at the top surface, a grip region at the first side surface, and a longitudinal groove oriented along the longitudinal axis at the bottom surface and extending from the front end to the back end. The longitudinal groove can be configured to snap onto and hold a surgical catheter therein.

In various detailed embodiments, the surgical apparatus can be configured for use with an augmented reality system, can be configured to function as a surgical fiducial marker localizer and also as a surgical catheter positioner, and/or can be configured to be handheld and used manually by a surgeon during a surgical procedure. The surgical apparatus can also include one or more arms extending laterally from the elongated main body, and each of the one or more arms can include one or more additional fiducial marker sites configured to host one or more additional fiducial markers at a top surface thereof. The one or more arms can be integrally formed with the elongated main body. In specific arrangements, the two arms can extend from the back end of the elongated main body on opposite sides of the longitudinal axis. All fiducial marker sites can be arranged in a pattern that is asymmetrical with respect to the longitudinal axis, and there can be a total of four fiducial marker sites. Each fiducial marker site can be configured to removably couple to an infrared reflective sphere as a fiducial marker.

In further detailed embodiments, the elongated main body can also include an indentation at the second side surface proximate and opposite to the grip region, which can further facilitate a handheld grip of the surgical apparatus. The elongated main body can further include a pointed nose at the top surface of the front end. The distances between the pointed nose and each fiducial marker site and the distances between all fiducial marker sites can all remain constant during a surgical procedure. In some arrangements, the pointed nose can be configured to contact a patient. The longitudinal groove can end beneath the pointed nose and can be configured to position a front end of the surgical catheter directly beneath the pointed nose to facilitate orientation of the catheter with respect to the patient.

In various further embodiments of the present disclosure, a system configured for use in augmented reality aided surgery can include a surgical catheter snap tool, one or more fiducial markers, and a surgical catheter. The surgical catheter snap tool can have an elongated main body defining a longitudinal axis and having a front end, a back end, a top surface, first and second side surfaces, and a bottom surface. The elongated main body can include one or more fiducial marker sites at the top surface, a grip region at the first side surface, and a longitudinal groove oriented along the longitudinal axis at the bottom surface and extending from the front end to the back end. The one or more fiducial markers can be coupled to the one or more fiducial marker sites, and the surgical catheter can be held within the longitudinal groove.

In various detailed embodiments, the system can include a stylet slidably inserted within the surgical catheter. Such a stylet can be configured to slide forward and backward within the surgical catheter, and the surgical catheter can be held in place within the longitudinal groove such that it does not slide or move therein during a surgical procedure. In some arrangements, the surgical catheter snap tool can further include one or more arms extending laterally from the elongated main body. Each of the one or more arms can include one or more additional fiducial marker sites configured to host one or more additional fiducial markers at a top surface thereof. The system can be configured for use with a separate augmented reality system, can be configured to function as a surgical fiducial marker localizer, can be configured to function as a surgical catheter positioner, and/or can be configured to be handheld and used manually by a surgeon during a surgical procedure.

In still further embodiments, a snap tool configured for use in augmented reality aided surgery can include an elongated main body defining a longitudinal axis and having a front end, back end, top surface, first and second side surfaces, and bottom surface. The elongated main body can include one or more fiducial marker sites configured to host fiducial markers, a grip region at the first side surface, and a longitudinal groove oriented along the longitudinal axis at the bottom surface and extending from a closed back end to an open front end. The longitudinal groove can be configured to snap onto and hold a cylindrically shaped object therein.

Other apparatuses, methods, features, and advantages of the disclosure will be or will become apparent to one with skill in the art upon examination of the following figures and detailed description. It is intended that all such additional apparatuses, methods, features and advantages be included within this description, be within the scope of the disclosure, and be protected by the accompanying claims.

BRIEF DESCRIPTION OF THE DRAWINGS

The included drawings are for illustrative purposes and serve only to provide examples of possible structures, arrangements, and methods of use for surgical catheter snap tools and related system components. These drawings in no way limit any changes in form and detail that may be made to the disclosure by one skilled in the art without departing from the spirit and scope of the disclosure.

DETAILED DESCRIPTION

Figure 1:
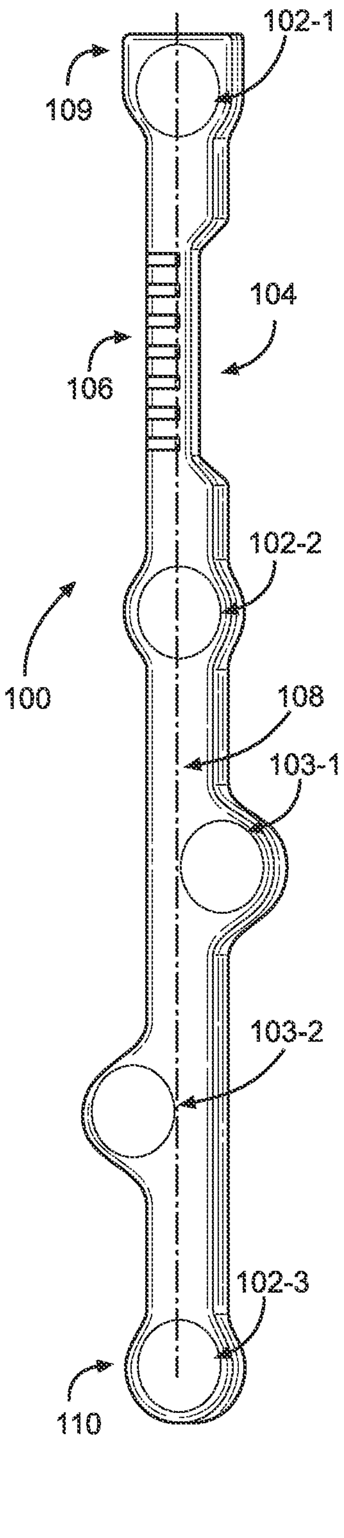
FIG. 1 illustrates in perspective view an example physical instrument according to one embodiment of the present disclosure.

Exemplary applications of apparatuses, systems, and methods according to the present disclosure are described in this section. These examples are being provided solely to add context and aid in the understanding of the disclosure. It will thus be apparent to one skilled in the art that the present disclosure may be practiced without some or all of these specific details provided herein. In some instances, well known process steps have not been described in detail in order to avoid unnecessarily obscuring the present disclosure. Other applications are possible, such that the following examples should not be taken as limiting. In the following detailed description, references are made to the accompanying drawings, which form a part of the description and in which are shown, by way of illustration, specific embodiments of the present disclosure. Although these embodiments are described in sufficient detail to enable one skilled in the art to practice the disclosure, it is understood that these examples are not limiting, such that other embodiments may be used, and changes may be made without departing from the spirit and scope of the disclosure.

The present disclosure relates in various embodiments to features, apparatuses, systems, and methods of use for surgical tools configured for use with augmented reality systems. This can involve localizer tools configured for the positioning of fiducial markers during augmented reality aided surgery, as well as catheter tools configured for the steady handling of surgical catheters. In specific arrangements, this can involve surgical catheter snap tools that combine the ability to position fiducial markers locally relative to a patient while also facilitating the steady handling and positioning of a surgical catheter with the same device.

In various embodiments of the present disclosure, novel surgical catheter snap tools can include an elongated main body having a grip region, a longitudinal groove configured to snap onto and hold a catheter therein, and one or more fiducial marker sites configured to host fiducial markers thereat. One or more arms can extend from the elongated main body, and each arm can include one or more additional fiducial marker sites configured to host additional fiducial markers. A surgical catheter snap tool can stand alone as a single device or can be part of a system that includes fiducial markers coupled to the fiducial marker sites, a catheter within the groove, and/or a stylet slidably inserted within the catheter.

Although various embodiments disclosed herein discuss surgical catheter snap tools in conjunction with catheters for introducing cutting stylets and infrared reflective spheres, it will be readily appreciated that other types of catheters, inner catheter medical devices, and fiducial markers can also be used with the disclosed surgical catheter snap tools. Other items beyond catheters can also be held within snap tool grooves, such as laser pointers, pens, and other writing instruments and tools. Other device shapes and alternative patterns to the arrangement of fiducial markers are also possible. Other applications, uses, arrangements, and extrapolations beyond the illustrated embodiments are also contemplated.

Referring first to FIG. 1, an example physical instrument is shown in perspective view. As shown in FIG. 1, according to various embodiments, a plurality of reflectors 102-1, 102-2, 102-3 and a plurality of off-set reflectors 103-1, 103-2 are disposed on a top surface 100 of the physical instrument. One or more of the reflectors 102-1, 102-2, 102-3 and the offset off-set reflectors 103-1, 103-2 may be made of a reflective material suitable for being tracked by an infrared camera(s).

A first side of the physical instrument includes an indentation 104 and a second side includes a grip region 106. The grip region 106 may include one or more grip ridges. Respective portions of each of the grip ridges may extend from the second side to the top surface 100 as well. The indentation 104 is formed by one or more portions of the first side of the physical instrument.

In one or more embodiments, the indentation 104 may have dimensions suitable for at least a portion of a human thumb to be positioned within the indentation 104. In some embodiments, the grip region 106 may have the dimensions and a number of grip ridges suitable for at least a portion of a human index finger to be positioned upon at least a portion of the grip region 106. It follows, then, that an individual, who is left-handed, may hold the physical instrument by performing and maintaining a pinched hand position with their thumb situated within the indentation 104 and their index finger placed upon the grip region 106. However, a right-handed individual will hold the physical instrument by performing and maintaining a pinched hand position with their thumb placed upon the grip region 106 and their index finger situated within the indentation 104.

The physical instrument has a defined central axis 108 that runs from a first terminal end 109 of the physical instrument to a second terminal end 110 of the physical instrument. Each reflector 102-1, 102-2, 102-3 includes a center and each respective reflector center is positioned on the top surface 100 in an alignment with the central axis 108. In some embodiments, one or more of the reflectors 102-1, 102-2, 102-3 may be disposed on the top surface 100 such that the central axis 108 bifurcates one or more of the reflectors 102-1, 102-2, 102-3. Each off-set reflector 103-1, 103-2 includes a center that is positioned on the top surface 100 in a misalignment with the central axis 108. In some embodiments, the central axis 108 does not bifurcate one or more of the off-set reflectors 103-1, 103-2.

In other embodiments, one or more of the off-set reflectors 103-1, 103-2 includes a center that is positioned on the top surface 100 in a misalignment with the central axis 108 such the central axis 108 may be positioned adjacent to an edge of one or more of the off-set reflectors 103-1, 103-2. In other embodiments, one or more of the off-set reflector 103-1, 103-2 includes a center that is positioned on the top surface 100 in a misalignment with the central axis 108 such the central axis 108 does not run through any portion of the one or more of the off-set reflectors 103-1, 103-2. In some embodiments, a first off-set reflector 103-1 may be more proximate to the first side than a second off-set reflector 103-2, whereby the second off-set reflector 103-2 may be more proximate to the second side than the first off-set reflector 103-1. In some embodiments, the central axis 108 is orientated such that it runs between a plurality of off-set reflectors 103-1, 103-2.

In other embodiments, respective portions of both the indentation 104 and the grip region 106 may be situated across from each other. In some embodiments, the indentation 104 and the grip region 106 may be situated across from each other in their entireties. In some embodiments, the entirety of the indentation 104 may be situated across from a portion of the grip region 106. In some embodiments, the indentation 104 may be situated across from the entirety of the grip region 106.

The indentation 104 and the grip region 106 may both be situated between a plurality of reflectors 102-1, 102-2. In other embodiments, the indentation 104 and the grip region 106 may both be situated between a plurality of off-set reflectors. In other embodiments, the indentation 104 and the grip region 106 may both be situated between a reflector and an off-set reflector.

Figure 2:
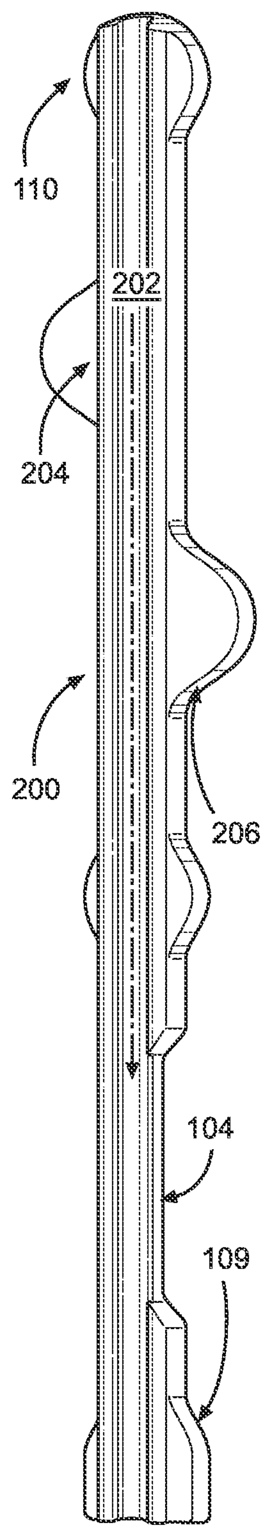
FIG. 2 illustrates in perspective view an example physical instrument according to one embodiment of the present disclosure.

As shown in FIG. 2, the physical instrument includes a bottom surface 200 with a groove 202 that runs along the bottom surface 200 from the first terminal end 109 to the second terminal end 110. In some embodiments, the groove 202 is aligned with the central axis 108 of the physical instrument. The bottom surface 200 includes a first bottom portion 206 that corresponds to the first off-set reflector 103-1 and a second bottom portion 204 that corresponds to the second off-set reflector 103-2.

The groove 202 has dimensions suitable for attaching another instrument to the physical instrument. For example, a tubular instrument may be attached to the physical as a result of inserting a portion of the tubular instrument within the groove 202. In some embodiments, dimensions of the groove 202 allow for the placement of at least a portion of a catheter within, along and throughout the groove 202. For example, dimensions of the groove 202 allow for at least a portion of a catheter to snap into the groove 202. In some embodiments, when a portion of catheter is positioned within the groove 202, an individual may hold the physical instrument while performing and maintaining a pinched hand position with their thumb (or index finger) situated within the indentation 104 and their index finger (or thumb) placed upon the grip region 106. By maintaining the pinched hand position, with respect to the indentation 104 and upon the grip region 106, the individual may thereby maintain control of the physical instrument in order to guide a catheter while it has been snapped into the groove 202. In addition, the indentation 104 further allows for an individual to place their thumb (or index finger) in the indentation 104 in such a manner that their pinched hand position will be in contact with both the physical instrument and the catheter (or any other type of instrument) while it has been snapped into the groove 202.

As the individual manipulates the physical instrument, the various changes to respective positions and orientations of the physical instrument are tracked via a camera tracking the reflectors 102-1, 102-2, 102-3, 103-1, 103-2. The respective positions and orientations of the physical instrument, tracked in reference to the reflectors 102-1, 102-2, 102-3, 103-1, 103-2, thereby serves as indications of a current placement and manipulation of the catheter as well. It is understood that dimensions of the groove 202 are not limited to being compatible with only tubular instruments. Various embodiments of the physical instrument may have a groove 202 with dimensions suitable for attaching the physical instrument to any instrument of any type of shape(s).

Figure 3:
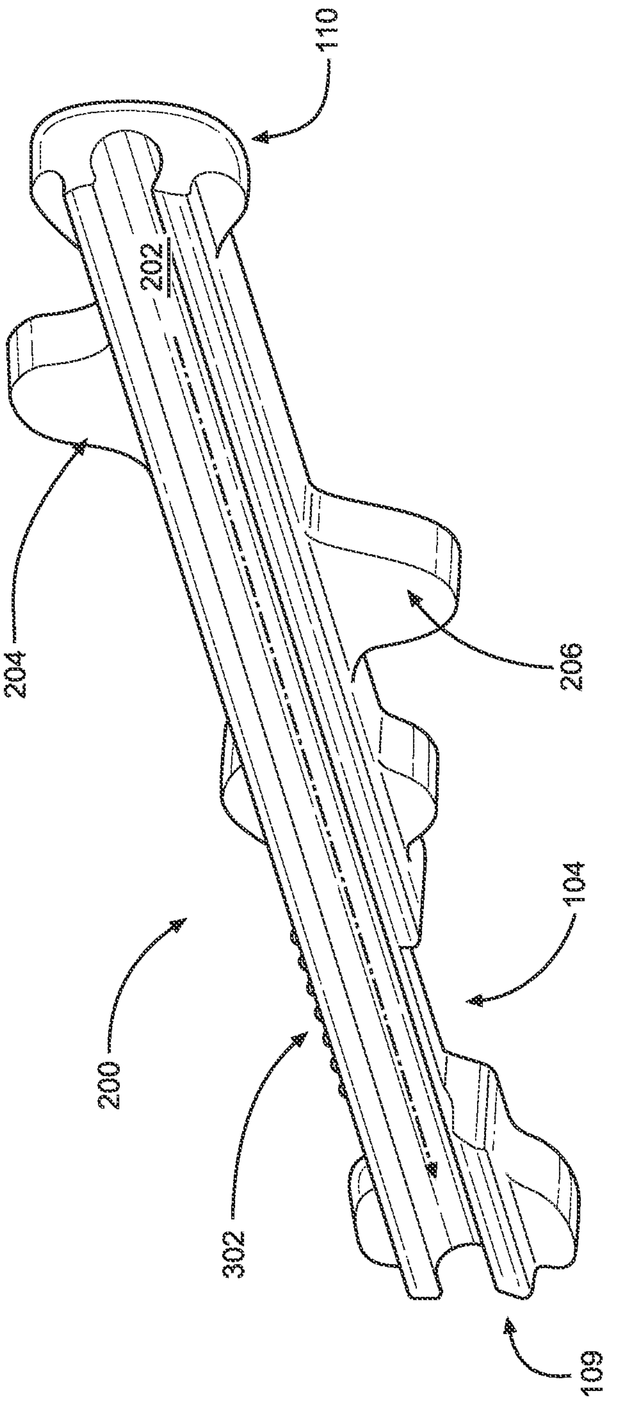
FIG. 3 illustrates in perspective view an example physical instrument according to one embodiment of the present disclosure.

As shown in FIG. 3, while one or more of the grip ridges of the grip region 106 may be disposed on the top surface 100, various portions of one or more of the grip ridges may extend to being disposed on at least a portion 302 of the second side. For example, one or more of the grip ridges of the grip region 106 may have a first ridge portion disposed on a portion 302 of the second side and also have a second ridge portion disposed on the top surface 100. In some embodiments, a terminus of one or more of the grip ridges of the grip region 106 may be positioned along the central axis 108. In some embodiments, a terminus of one or more of the grip ridges of the grip region 106 may not be positioned along the central axis 108.

Figure 4A:
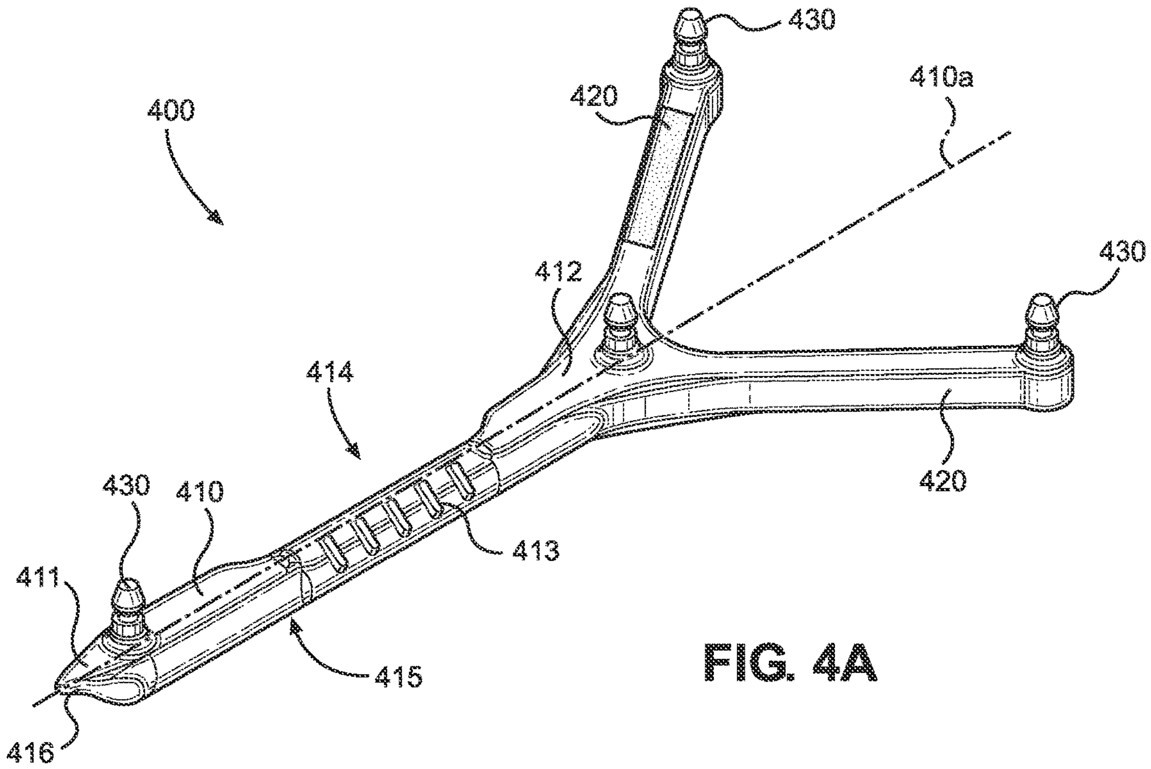
FIG. 4A illustrates in top perspective view an example surgical catheter snap tool according to one embodiment of the present disclosure.
Figure 4B:
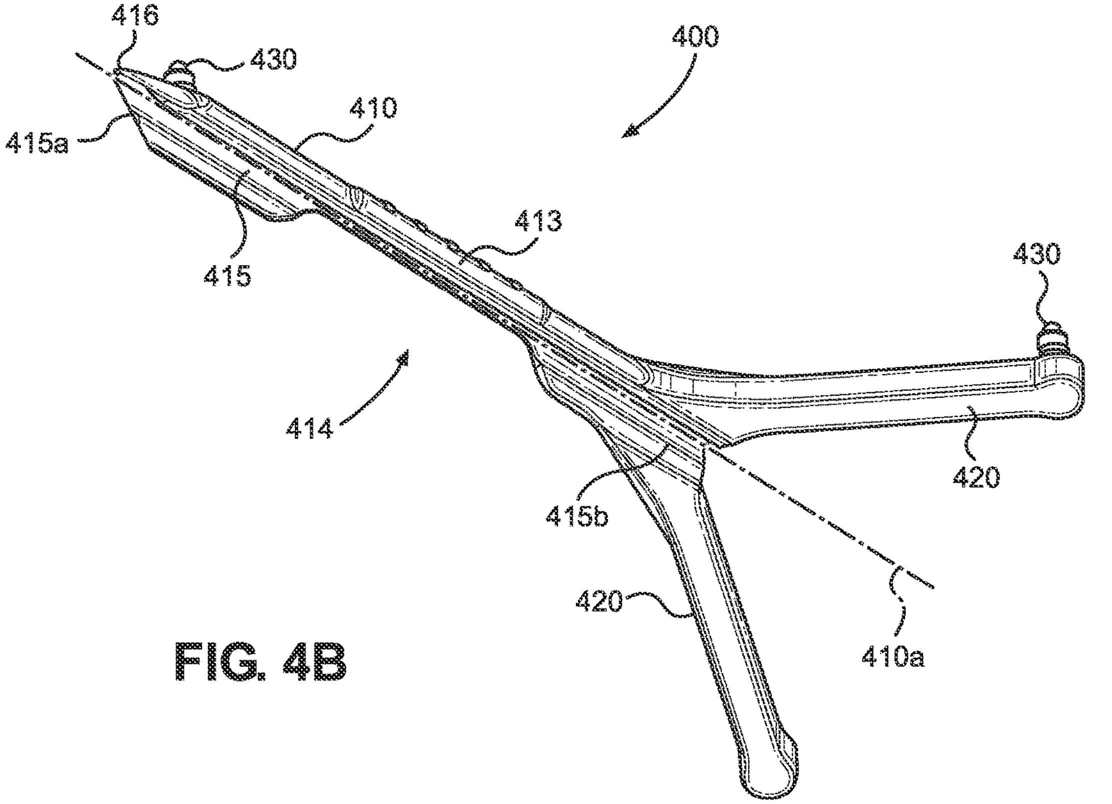
FIG. 4B illustrates in bottom perspective view the surgical catheter snap tool of FIG. 4A according to one embodiment of the present disclosure.

Transitioning now to FIGS. 4A and 4B, an example surgical catheter snap tool is illustrated in top perspective and bottom perspective views respectively. Surgical catheter snap tool 400 can be similar to the above physical instrument in some regards. For example, surgical catheter snap tool 400 can be configured to be hand held, can be configured for use with surgical fiducial markers, and can be configured to hold a catheter or other tubular surgical instrument therein. Surgical catheter snap tool 400 can specifically be used as a surgical catheter positioner and also as a fiducial marker localizer in conjunction with a separate augmented reality system.

In various embodiments, a given surgical catheter snap tool 400 can include an elongated main body 410 having a top surface, first and second side surfaces, and a bottom surface. The top surface is shown in FIG. 4A, while the bottom surface is shown in FIG. 4B. Main body 410 can define a longitudinal axis 410*a* therethrough, and can have a front end 411, a back end 412, a grip region 413 at a first side surface, and an indentation 414 at a second side surface proximate and opposite to the grip region, similar to the above physical instrument. Main body 410 can also include one or more fiducial marker sites 430 configured to host fiducial markers at its top surface, such as at front end 411 and back end 412, as shown.

Main body 410 can also include a longitudinal channel or groove 415 oriented along longitudinal axis 410*a* at its bottom surface, and this longitudinal groove can extend from front end 411 to the back end 412 in some arrangements. In some arrangements, longitudinal groove 415 can be configured to snap onto and hold a surgical catheter therein. As such, groove 415 can be sized and shaped according to the size and shape of one more surgical catheters, such as by having a partial tubular shape with a diameter that matches the outer diameter of a tubular catheter having an internal channel. As shown, longitudinal groove 415 can include an opening along some or all of its bottom surface to facilitate snapping a catheter in place and also removing the catheter from the groove. Main body 410, or at least its region surrounding groove 415, can be formed from a material having enough flexibility to snap a catheter into the groove such that the catheter is then fixed in place with respect to the groove and the overall surgical catheter snap tool 400. This can include, for example, a hard polymer or rubber material, among other possible materials. Alternatively, or in addition, a catheter or other suitable instrument or item can be slid into longitudinal groove 415 from the front end or back end of the groove.

Main body 410 can also include a pointed nose 416 at front end 411, and this pointed nose can extend from the front end along longitudinal axis 410*a*. In some embodiments, pointed nose 416 can have a blunted tip or other suitable feature such that it is configured to contact a patient safely or to contact another item to be referenced during a surgical procedure involving an augmented reality system. In some arrangements, pointed nose 416 can be configured to function as a localizer feature that can facilitate interaction between virtual and physical spaces as surgical catheter snap tool 400 is used during a procedure involving a separate augmented reality system. For example, the distances between pointed nose 416 and some or all fiducial markers coupled to fiducial marker sites 430 can all remain at known constants during a surgical procedure, such that the front edge of pointed nose 416 can serve as a known reference location as the separate augmented reality system interacts with the fiducial markers. Of course, the distances between some or all fiducial markers coupled to fiducial marker sites 430 can also remain at known constants during a procedure, as will be appreciated by those of skill in the art. Other shapes, sizes, directions, and locations are also possible for pointed nose 416, and it will be understood that such other variations and/or other features on surgical catheter snap tool 400 can also or alternatively serve as known reference points to facilitate a localizer function of the tool.

Longitudinal groove 415 can end beneath pointed nose 416 and can be configured to position a front end or front region of a surgical catheter held therein directly beneath the pointed nose to facilitate orientation of the catheter with respect to a patient during a surgical procedure. The surgical catheter can have a front end located at or proximate pointed nose 416, or the front end of the catheter can extend at a distance past the pointed nose such that a front region of the catheter is at the pointed nose, as shown in system 600 below. As seen in FIG. 4B, longitudinal groove 415 can have a front opening 415*a* beneath pointed nose 416 and through the front end of main body 410 and overall surgical catheter snap tool 400. Longitudinal groove 415 can also have a back opening 415*b* through the back end of main body 410, such that the longitudinal groove extends along the entire length of the main body. Other arrangements can have a groove that does not extend along the entire length of the main body, as detailed below.

Surgical catheter snap tool 400 can also include one or more arms 420 extending laterally from elongated main body 410. Each arm 420 can include an additional one or more fiducial marker sites 430 configured to host one or more additional fiducial markers at its top surface. In some arrangements, fiducial markers can include infrared reflective spheres configured for use with an augmented reality system, and some or all fiducial marker sites 430 on main body 410 and each arm 420 can be posts specifically configured for the removable coupling of such infrared reflective spheres. Other types of fiducial marker sites and/or fiducial markers are also possible, such as those provided in the physical instrument set forth above in FIGS. 1-3, for example.

In some arrangements, arms 420 can be integrally formed with elongated main body 410 for a unitary surgical catheter snap tool body, although these can be separate items coupled together in any suitable manner. As illustrated in FIGS. 4A-4B, arms 420 can include two arms that extend from back end 412 of elongated main body 410 on opposite sides of longitudinal axis 410*a*, and these arms can be asymmetrical with respect to each other. As such, all fiducial marker sites 430 on surgical catheter snap tool 400 can be arranged in an overall pattern that is asymmetrical with respect to longitudinal axis 410*a*, which can be advantageous in reducing errors or confusion in an augmented reality system interacting with fiducial markers coupled at the fiducial marker sites. While exactly four fiducial marker sites 430 are shown on surgical catheter snap tool 400 in the illustrative example provided herein, it will be understood that more or fewer fiducial marker sites may alternatively be used, and that the locations of and distances between these sites may vary without detracting from their overall functionality.

Continuing with FIGS. 5A-5D, an example surgical catheter snap tool in depicted in top plan, side elevation, bottom plan, and rear elevation views respectively. Surgical catheter snap tool 500 can be identical or substantially similar to the surgical catheter snap tool 400 illustrated and described above. As such, surgical catheter snap tool 500 can generally include an elongated main body 510, one or more arms 520 extending therefrom, and one or more fiducial marker sites 530 on the main body, one or more arm(s), or any combination thereof. Main body 510 can similarly define a longitudinal axis therethrough and can similarly have a front end, back end, grip region 513 at a first side surface, and indentation 514 at a second side that can combine with the grip region to facilitate a good handheld grip of the main body and overall surgical catheter snap tool 500.

Figure 5A:
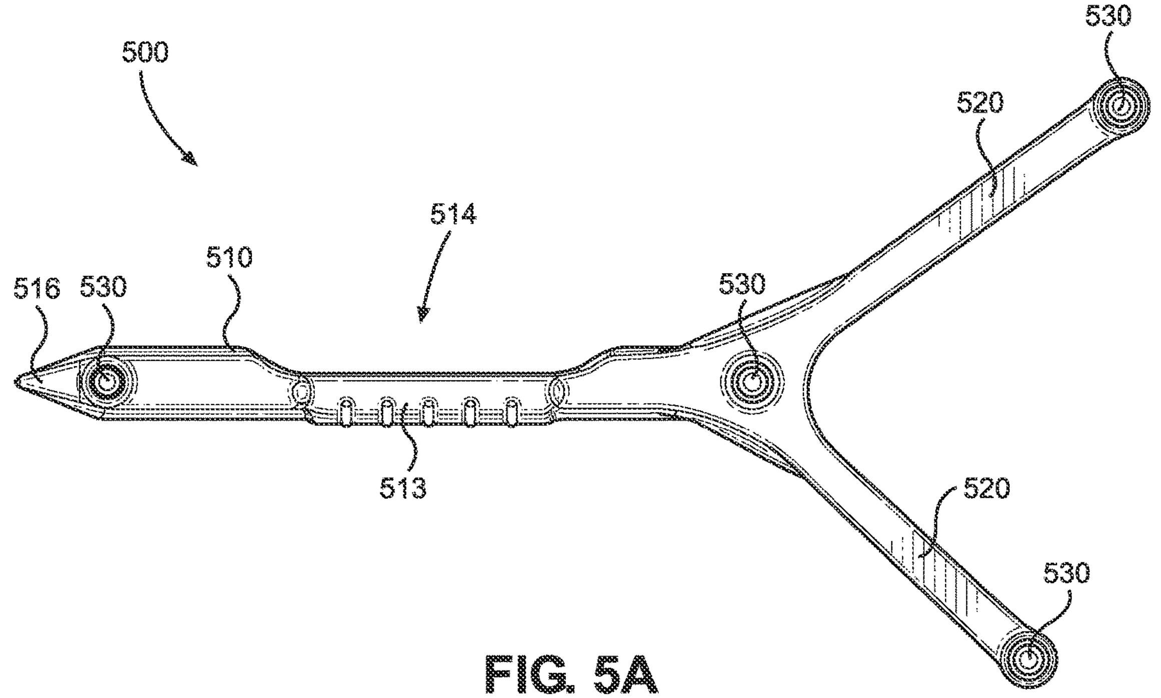
FIG. 5A illustrates in top plan view an example surgical catheter snap tool according to one embodiment of the present disclosure.
Figure 5B:
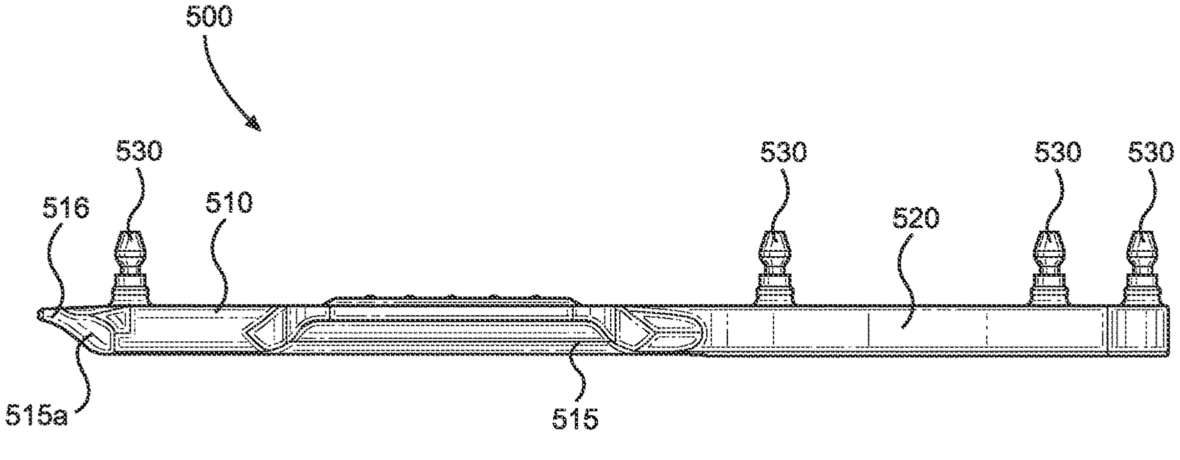
FIG. 5B illustrates in side elevation view the surgical catheter snap tool of FIG. 5A according to one embodiment of the present disclosure.
Figure 5C:
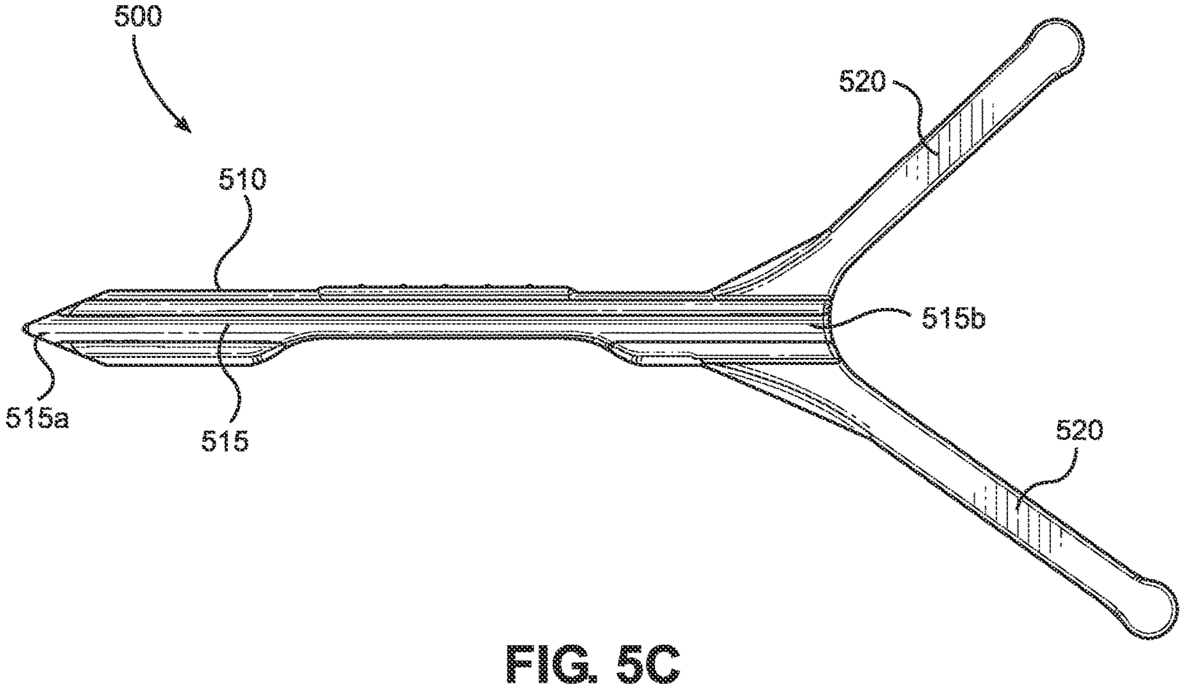
FIG. 5C illustrates in bottom plan view the surgical catheter snap tool of FIG. 5A according to one embodiment of the present disclosure.
Figure 5D:
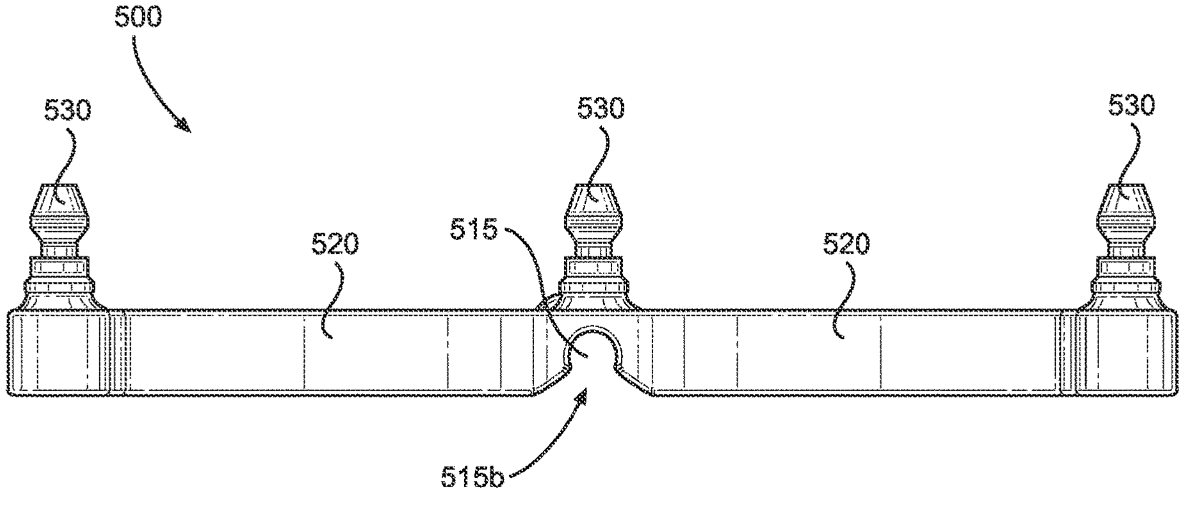
FIG. 5D illustrates in rear elevation view the surgical catheter snap tool of FIG. 5A according to one embodiment of the present disclosure.
Figure 6A:
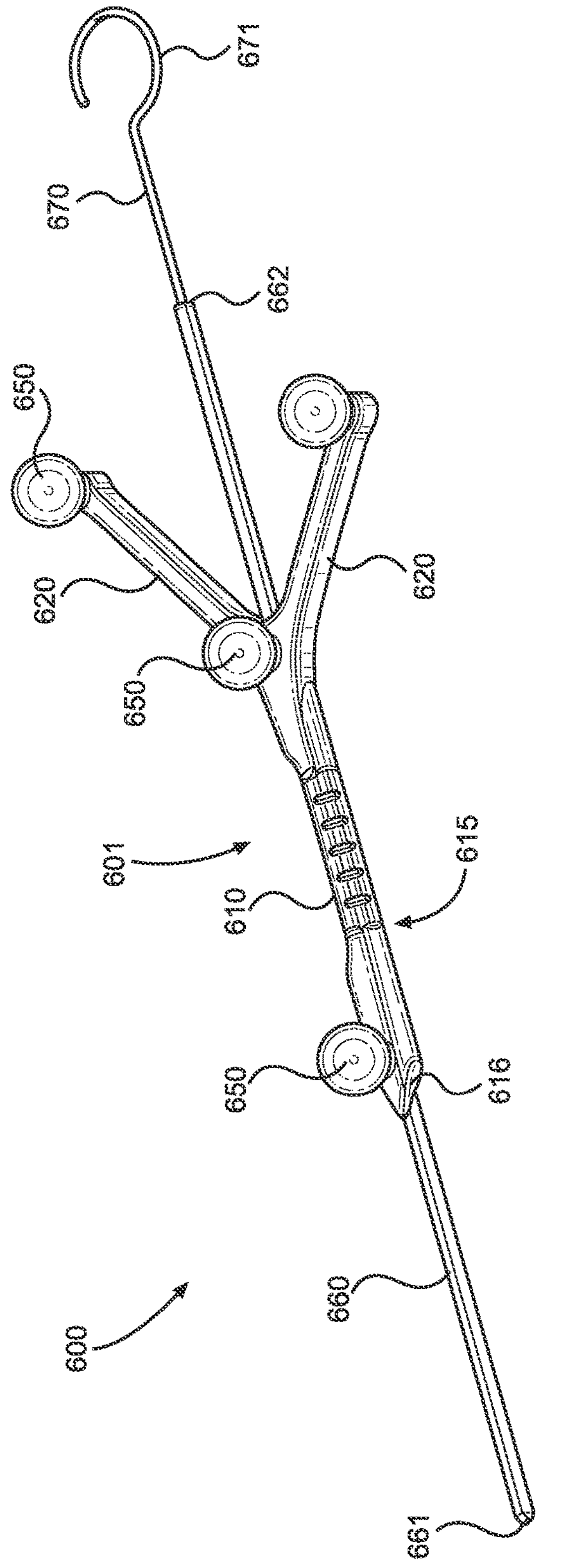
FIG. 6A illustrates in top perspective view an example surgical system configured for use in augmented reality aided surgery according to one embodiment of the present disclosure.
Figure 6B:
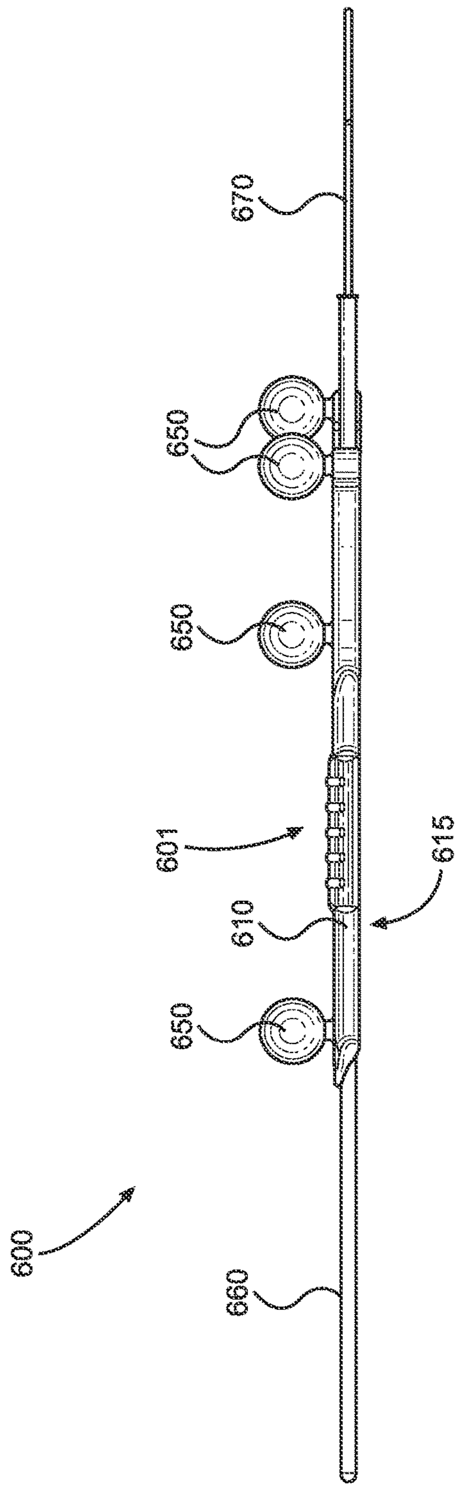
FIG. 6B illustrates in side elevation view the surgical system of FIG. 6A according to one embodiment of the present disclosure.
Figure 6C:
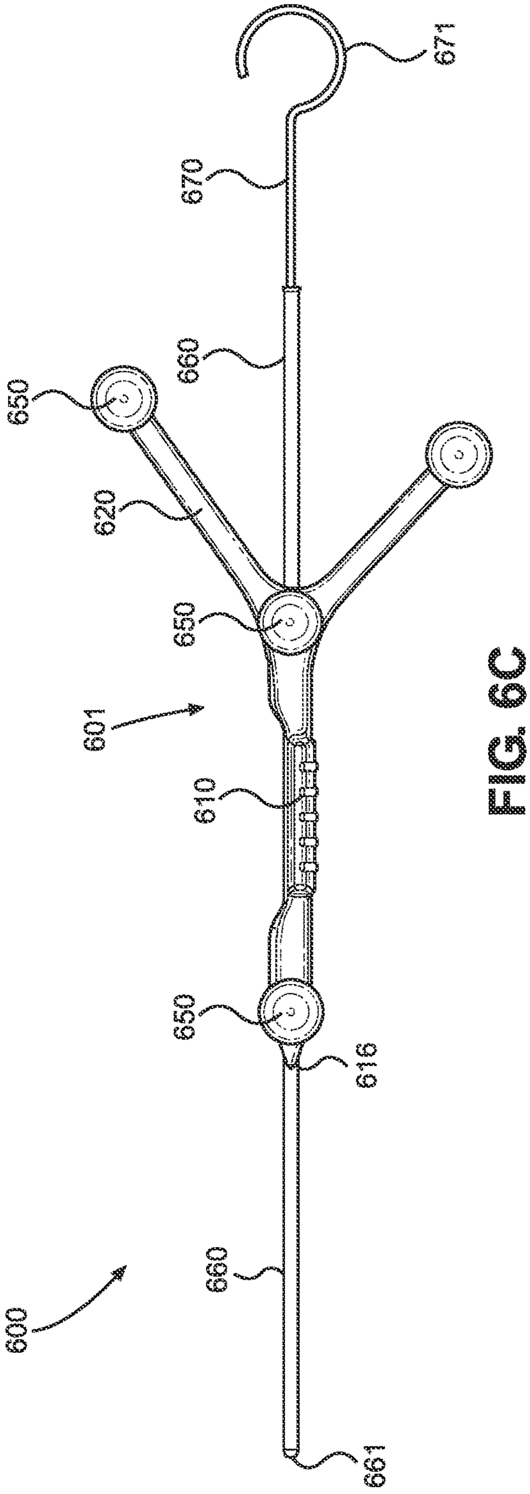
FIG. 6C illustrates in top plan view the surgical system of FIG. 6A according to one embodiment of the present disclosure.
Figure 6D:
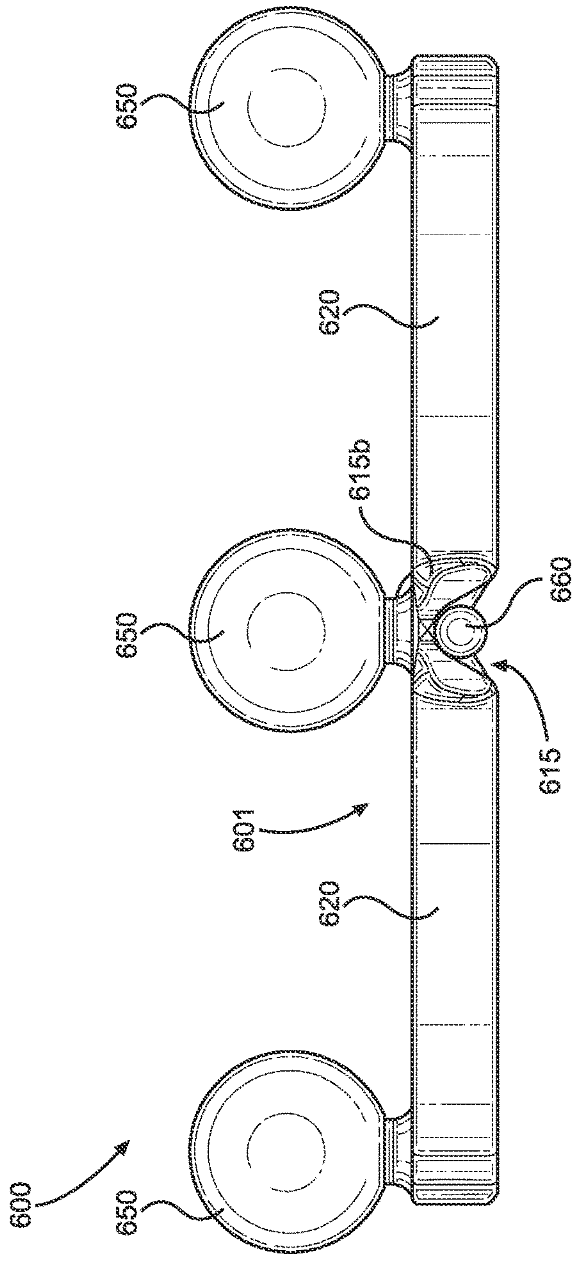
FIG. 6D illustrates in rear elevation view the surgical system of FIG. 6A according to one embodiment of the present disclosure.

Main body 510 can also include a longitudinal channel or groove 515 oriented along its longitudinal axis at its bottom surface, as well as a pointed nose 516 at its front end, both of which can be identical or substantially similar to corresponding features in snap tool 400 set forth above. Longitudinal groove 515 can similarly have a front opening 515*a* beneath pointed nose 516 and through the front end of main body 510 and a back opening 515*b* through the back end of the main body, such that the longitudinal groove extends along the entire length of the main body and through both distal ends thereof. As can be seen in FIGS. 5B and 5C, this longitudinal groove 515 can be visible and can even be accessed along at least one side of main body 510, such as where indentation is location 514. This can allow a surgeon or other operator to contact or press directly against a catheter or other item located within groove 515 while holding and using surgical catheter snap tool 500.

As in the foregoing example, longitudinal groove 515 can be configured to snap onto and hold a surgical catheter or any other suitable tubular or cylindrically shaped item therein, and this groove can be sized and shaped according to the size and shape of any specific catheters, devices, or other instruments that are to be snapped into and removably held therein. Again, an opening along some or all of the bottom of longitudinal groove 515 can facilitate snapping in place and also removing a suitably sized catheter or other cylindrically shaped object. As can be seen in the rear elevation view of FIG. 5D, longitudinal groove 515 can extend from its back opening 515*b* all the way through the rest of the main body of surgical catheter snap tool 500, and this groove can have a geometry that facilitates a removable snap fit and firm hold for a catheter or other suitable instrument or object therein. For example, longitudinal groove 515 can have a geometry along some or all of its length that includes a closed top surface and curved or cylindrically shaped sidewalls that extend past a halfway point toward a bottom opening, such that a catheter or other object can be snapped into the bottom opening and then held in place by the lower portions of the sidewalls. Other groove geometries and arrangements are also possible, as will be readily appreciated. Other details, and features of surgical catheter snap tool 500 can be identical or similar to those in above snap tool 400.

Next, FIGS. 6A-6D illustrate an example surgical system configured for use in augmented reality aided surgery in top perspective, side elevation, top plan, and rear elevation views respectively. Surgical system 600 can include a surgical catheter snap tool 601, multiple fiducial markers 650, a surgical catheter 660, and a stylet 670. Surgical catheter snap tool 601 can be identical or substantially similar to surgical catheter snap tools 400 and/or 500 above, and as such can include an elongated main body 610, one or more arms 620 extending therefrom, one or more fiducial marker sites on the main body and/or the arm(s), a longitudinal groove 615 along the main body bottom, a pointed nose 616 at the main body front end, and various other features and details disclosed and illustrated above. Fiducial markers 650 can be removably coupled to the fiducial marker sites on surgical catheter snap tool 601, and these fiducial markers can be infrared reflective spheres, for example, although other types of fiducial markers can alternatively or additionally be used.

Surgical catheter 660 can be snapped into and held within longitudinal groove 615 such that it extends through the full length of the groove. A front end 661 of surgical catheter 660 can extend through and beyond a front opening of longitudinal groove 615 and can also extend past the front end of main body 610. Front end 661 can have an opening configured to allow an internal component to extend from a hollow region within surgical catheter 660. A back end 661 of surgical catheter 660 can extend through and beyond a back opening 615*b* of longitudinal groove 615 and can also extend past the back end of main body 610. Back end 662 can have an opening configured to allow an internal component to be inserted into and extend from a hollow region within surgical catheter 660.

A surgical probe, cutting tool, or other suitable item such as a stylet 670 can be slidably inserted into a hollow region within surgical catheter 660. Stylet 670 can be a manually operatable tool having an elongated shaft that can slide within surgical catheter 660, a tool or other feature on a front portion of the elongated shaft that can extend from an opening at the front end 661 of the catheter, and a ring or handle 671 at a rear portion of the elongated shaft that can be used to manually control and manipulate the stylet. For example, handle 671 can be used to slide stylet 670 forward and backward within surgical catheter 660, and may also facilitate rotational motion of the stylet within the catheter. Stylet 670 can be configured to be inserted into a hollow region within surgical catheter 660 at an opening at the back end 662 of the catheter, although other configurations are possible. In some arrangements, pressure can be manually applied onto surgical catheter 660 through a side opening or indentation along main body 610, which can result in holding stylet 670 in place within surgical catheter 660. Since surgical catheter 660 can ordinarily be snapped into longitudinal groove 615 such that the catheter does not slide or move within the groove (i.e., with respect to overall snap tool 601, this can result in stylet 670 also not sliding or moving with respect to the groove or overall snap tool while manual pressure is applied to the catheter to a side opening along main body 610.

Figure 7A:
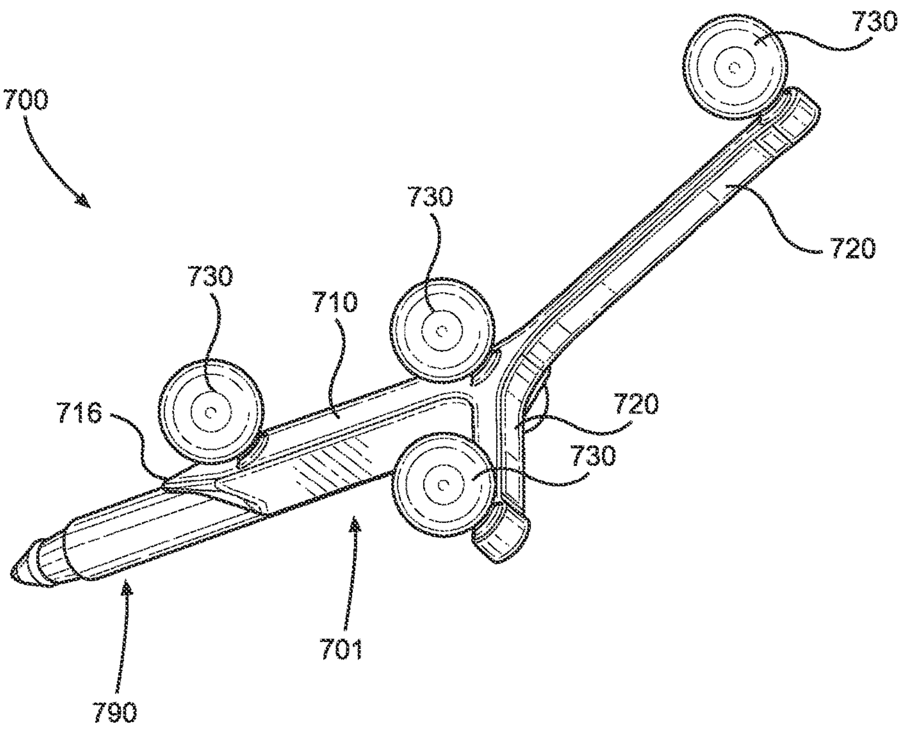
FIG. 7A illustrates in top rear perspective view an example snap tool holding a writing instrument according to one embodiment of the present disclosure.
Figure 7B:
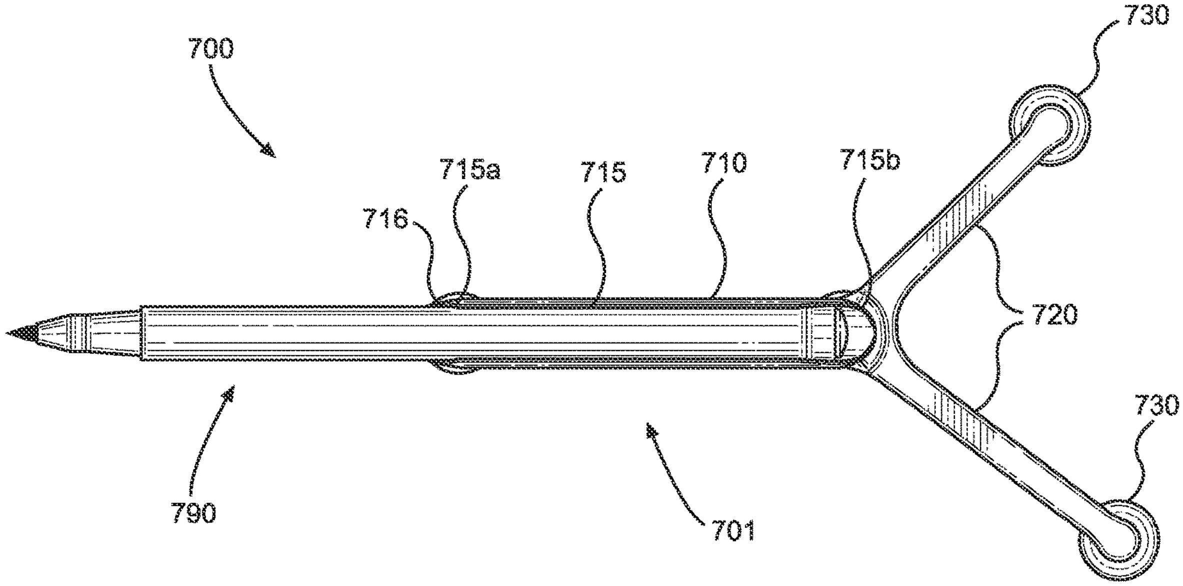
FIG. 7B illustrates in bottom plan view the snap tool of FIG. 7A according to one embodiment of the present disclosure.
Figure 7C:
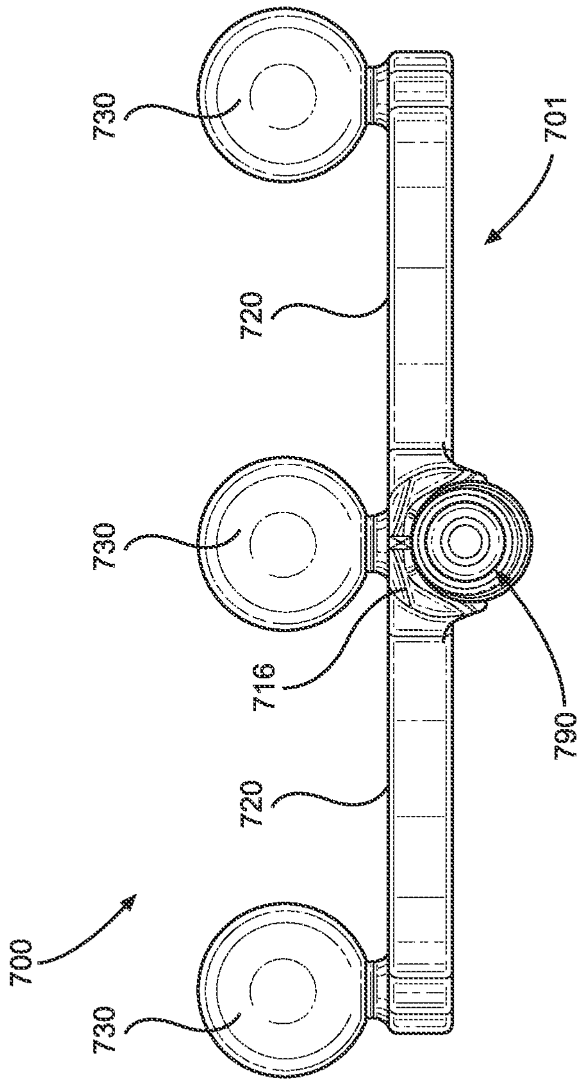
FIG. 7C illustrates in front elevation view the snap tool of FIG. 7A according to one embodiment of the present disclosure.

Lastly, FIGS. 7A-7C depict an example snap tool holding a writing instrument in top rear perspective, bottom plan, and front elevation views respectively. Arrangement 700 can include a snap tool 701 and a separate writing instrument 790 held within the snap tool. Snap tool 701 can be similar in some regards to the various surgical catheter snap tools 400, 500, and 601 illustrated and described in detail above. For example, snap tool 701 can include an elongated main body 710, one or more arms 720, one or more fiducial markers 730, a pointed nose 716 at a front end of the main body, and a longitudinal groove 715 at a bottom of the main body extending along a longitudinal axis defined by the main body, among other components and features that are similarly found in the above embodiments. Similar to the foregoing examples, longitudinal groove 715 can be sized, shaped, and have a geometry suitable for snapping writing instrument 790 or any other suitable item in place to be held therein.

Also similar to the foregoing embodiments, longitudinal groove 715 can include a front opening **715*a* at a front end thereof, such that writing instrument 790 can extend past this front opening and the front end of main body 710 when the writing instrument is snapped into and held within the longitudinal groove. Unlike various foregoing embodiments, longitudinal groove 715 can have a closed back end 715*b* that does not extend through a back end of main body 710, such that the back end of writing instrument 790 cannot extend out of the main body. This groove arrangement can allow for a measured placement of writing instrument 790 within longitudinal groove 715, such as where a back end or other feature of the writing instrument encounters a hard physical stop within the groove at or proximate closed back end 715*b***.

Known distances on snap tool 701, such as between various fiducial markers 730 and other snap tool features, and well as a known distance between this back end or hard stop feature and the front tip of writing instrument 790 can then allow for tracking and accurate reference of where the front tip is located in augmented reality space. Other arrangements with a longitudinal groove having a closed front end and open back end, or a groove having both closed back and front ends can also be used for various purposes and designs as may be desired. Furthermore, other tubular or cylindrically shaped instruments, tools, or objects can be used instead of a writing instrument for a given snap tool 701. These can include, for example, pens, markers, laser pointers, drills, screw drivers, evacuators, introducers, and the like.

Although the foregoing disclosure has been described in detail by way of illustration and example for purposes of clarity and understanding, it will be recognized that the above described disclosure may be embodied in numerous other specific variations and embodiments without departing from the spirit or essential characteristics of the disclosure. Certain changes and modifications may be practiced, and it is understood that the disclosure is not to be limited by the foregoing details, but rather is to be defined by the scope of the appended claims.

What is claimed is:

1. A surgical apparatus, comprising:

an elongated main body defining a longitudinal axis and having a front end, a back end, a top surface, first and second side surfaces, and a bottom surface, wherein the elongated main body includes:

a plurality of fiducial marker sites configured to host a plurality of fiducial markers at the top surface, a grip region at the first side surface, and a longitudinal groove formed in the bottom surface of the elongated main body, oriented along the longitudinal axis, and extending from the front end to the back end of the elongated main body, wherein the longitudinal groove comprises a partial tubular shape with a diameter that matches the outer diameter of a surgical catheter configured to snap onto and hold the surgical catheter therein wherein the surgical catheter is held within the full length of the longitudinal groove and extends past the front end and the back end of the elongated main body, and wherein the surgical apparatus is configured for use with an augmented reality system.

2. The surgical apparatus of claim 1, wherein the surgical apparatus is configured to function as a surgical fiducial marker localizer to position the plurality of fiducial markers and also as a surgical catheter positioner to hold the surgical catheter at a secure position.

3. The surgical apparatus of claim 1, wherein the surgical apparatus is configured to be handheld and used manually by a surgeon during a surgical procedure.

4. The surgical apparatus of claim 1, further comprising: one or more arms extending laterally from the elongated main body, wherein each of the one or more arms includes one or more additional fiducial marker sites configured to host one or more additional fiducial markers at a top surface thereof.

5. The surgical apparatus of claim 4, wherein the one or more arms are integrally formed with the elongated main body.

6. The surgical apparatus of claim 4, wherein the one or more arms include two arms that extend from the back end of the elongated main body on opposite sides of the longitudinal axis.

7. The surgical apparatus of claim 4, wherein all fiducial marker sites are arranged in a pattern that is asymmetrical with respect to the longitudinal axis.

8. The surgical apparatus of claim 4, wherein there are a total of four fiducial marker sites.

9. The surgical apparatus of claim 1, wherein the one or more fiducial marker sites are each configured to removably couple to an infrared reflective sphere as a fiducial marker.

10. The surgical apparatus of claim 1, wherein the elongated main body further includes an indentation at the second side surface proximate and opposite to the grip region.

11. The surgical apparatus of claim 10, wherein the indentation is configured to allow access to the surgical catheter held within the longitudinal groove from the second side surface of the elongated main body.

12. The surgical apparatus of claim 1, wherein the elongated main body further includes a pointed nose at the top surface of the front end.

13. The surgical apparatus of claim 12, wherein the surgical apparatus is configured such that the distances between the pointed nose and each fiducial marker site and the distances between all fiducial marker sites all remain constant during a surgical procedure.

14. The surgical apparatus of claim 12, wherein the pointed nose of the elongated main body is configured to contact a patient and the longitudinal groove ends beneath the pointed nose and is configured to position a front end of the surgical catheter directly beneath the pointed nose to facilitate orientation of the catheter with respect to the patient.

15. The surgical apparatus of claim 1, wherein the portion of the elongated main body around the longitudinal groove is formed from a material having enough flexibility to facilitate snapping the surgical catheter into the longitudinal groove.

16. A system configured for use in augmented reality aided surgery, the system comprising:

a surgical catheter snap tool having an elongated main body defining a longitudinal axis and having a front end, a back end, a top surface, first and second side surfaces, and a bottom surface, wherein the elongated main body includes one or more fiducial marker sites at the top surface, a grip region at the first side surface, and a longitudinal groove formed in the bottom surface of the elongated main body, oriented along the longitudinal axis, and extending from the front end to the back end of the elongated main body;

one or more fiducial markers coupled to the one or more fiducial marker sites; and a surgical catheter held within the full length of the longitudinal groove and extending past the front end and the back end of the elongated main body, wherein the longitudinal groove comprises a partial tubular shape with a diameter that matches the outer diameter of the surgical catheter configured to snap onto and hold the surgical catheter, wherein the system is configured for use with an augmented reality system.

17. The system of claim 16, further comprising:

a stylet slidably inserted within the surgical catheter.

18. The system of claim 17, wherein the stylet is configured to slide forward and backward within the surgical catheter, and wherein the surgical catheter is held in place within the longitudinal groove such that it does not slide or move therein during a surgical procedure.

19. The system of claim 16, wherein the surgical catheter snap tool further includes one or more arms extending laterally from the elongated main body, and wherein each of the one or more arms includes one or more additional fiducial marker sites configured to host one or more additional fiducial markers at a top surface thereof.

20. A snap tool configured for use in augmented reality aided surgery, comprising:

an elongated main body defining a longitudinal axis and having a front end, a back end, a top surface, first and second side surfaces, and a bottom surface, wherein the elongated main body includes:

one or more fiducial marker sites configured to host fiducial markers, a grip region at the first side surface, and a longitudinal groove formed in the bottom surface of the elongated main body, oriented along the longitudinal axis, and extending from a closed back end to an open front end, wherein the longitudinal groove comprises a partial tubular shape with a diameter that matches the outer diameter of a cylindrically shaped surgical device configured to snap onto and hold the cylindrically shaped surgical device therein wherein the cylindrically shaped surgical device is held within the full length of the longitudinal groove and extends past the front end of the elongated main body, and wherein the snap tool is configured for use with an augmented reality system.

* * * * *